US006998387B1

(12) United States Patent
Goke et al.

(10) Patent No.: US 6,998,387 B1
(45) Date of Patent: Feb. 14, 2006

(54) HUMAN APPETITE CONTROL BY GLUCAGON-LIKE PEPTIDE RECEPTOR BINDING COMPOUNDS

(75) Inventors: Burkhard Goke, Gauting (DE); Christoph Beglinger, Basel (CH); Thomas R. Coolidge, Falls Village, CT (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/646,433

(22) PCT Filed: Mar. 16, 1999

(86) PCT No.: PCT/US99/05571

§ 371 (c)(1),
(2), (4) Date: Nov. 24, 2000

(87) PCT Pub. No.: WO99/47161

PCT Pub. Date: Sep. 23, 1999

Related U.S. Application Data (60) Provisional application No. 60/078,544, filed on Mar. 19, 1998.

(51) Int. Cl.
*A61K 38/00* (2006.01)
*A61K 38/26* (2006.01)

(52) U.S. Cl. .................. 514/12; 514/809; 530/308; 530/324

(58) Field of Classification Search .............. 514/12, 514/909; 530/308, 324
See application file for complete search history.

(56) References Cited

U.S. PATENT DOCUMENTS

| | | | |
|---|---|---|---|
| 5,120,712 A | 6/1992 | Habener | 514/12 |
| 5,631,224 A | 5/1997 | Efendic et al. | 514/12 |
| 6,191,102 B1 | 2/2001 | DiMarchi et al. | |
| 2003/0232754 A1 | 12/2003 | Holst et al. | |

FOREIGN PATENT DOCUMENTS

| | | | |
|---|---|---|---|
| WO | WO 97/31943 | * | 9/1997 |
| WO | WO 97/31943 A1 | | 9/1997 |
| WO | WO 98/19698 A1 | | 5/1998 |
| WO | WO 98/30231 | | 7/1998 |
| WO | WO 98/20895 | | 5/1999 |

OTHER PUBLICATIONS

Navarro et al., Journal Of Neurochemistry, vol. 67, No. 5, pp. 1982-1991, 1996.*
Turton et al., (Nature, vol. 379, pp, 69-72, Jan. 4, 1996.*
Furuse et al., Brain research, vol. 755, pp. 167-169, 1997.*
Furuse et al. Effects of Various N-terminal Fragments of Glucagon-Like Peptide-1(7-36) on Food Intake in the Neonatal Chick. Brain Research. 1998, vol. 807, pp. 214-217, see entire document.
Turton et al. A Role for Glucagon-Like Peptide 1 in the Central Regulation of Feeding. Nature. Jan. 4, 1996, vol. 379, pp. 69-72, see entire document.
Navarro et al. Colocalization of Glucagon-Like Peptide-1 (GLP-1) Receptors, Glucose Transporter GLUT-2, and Glucokinase mRNAs in Rat Hypothalamic Cells: Evidence for a Role of GLP-1 Receptor Agonists as inhibitory Signal for Food and Water Intake. Journal of Neurochemistry, 1996, vol. 67, No. 5, pp. 1982-1991, especially pp. 1982-1983 and 1988-1990.
Furuse et al. Intracerebroventricular Injection of Mammalian and Chicken Glucagon-Like Peptide-1 Inhibits Food Intake of the Neonatal Chick. Brain Research. 1997, vol. 755, pp. 167-169, see entire document.
Merran et al. Repeated Intracerebroventricular Administration of Glucagon-Like Peptide-1 (7-36) Amide or Exendin-(9-39) Alters Body Weight in the Rat. Endocrinology. 1999, vol. 140, No. 1, pp. 244-250, especially pp. 244 and 249.
Naslund et al. Glucagon-Like Peptide-1 Increases the Period of Postprandial Safety and Slows Gastric Emptying in the Obese Men. Am. J. Clin. Nutr. 1998, vol. 68, pp. 525-530, especially pp. 525 and 528.
Gutzwiller et al. Glucagon-Like Peptide-1: A Potent Regulator of Food Intake in Humans. Gut. 1999, vol. 44, pp. 81-86, especially pp. 81, and 84-85.
Billington, et al., "Appetite regulation: Shedding new light on obesity," Dispatch, Current Biology 1996, vol. 6 No. 8:920-923.

* cited by examiner

*Primary Examiner*—Jon Weber
*Assistant Examiner*—Abdel A. Mohamed
(74) *Attorney, Agent, or Firm*—Arnold & Porter, LLP (57) ABSTRACT

A composition including a compound which binds to a receptor for glucagon-like peptide-1 and a pharmaceutical carrier. The amount of the compound present is effective to control appetite in a human. Also disclosed is a method for controlling appetite and for reducing food intake in a human by administering to the human a composition comprising a compound which binds to a receptor for glucagon-like peptide-1 and a pharmaceutical carrier.

19 Claims, 7 Drawing Sheets

■ Meal
■ Insulin/Glucose
▲ OCK
● GLP-1/Leptin
× Visual analogue scales

Fig. 1

—□— Placebo
—○— GPL-1 0.375 pmol/kg/min
—△— GPL-1 0.75 pmol/kg/min
—▽— GPL-1 1.5 pmol/kg/min

HUMAN APPETITE CONTROL BY GLUCAGON-LIKE PEPTIDE RECEPTOR BINDING COMPOUNDS

CROSS REFERENCE TO RELATED APPLICATIONS

This application is a 371 of WO 99/47161, filed Mar. 16, 1999, which claims the benefit of U.S. Provisional Application Ser. No. 60/078,544, filed Mar. 19, 1998.

FIELD OF THE INVENTION

The present invention relates to the field of appetite control, and more particularly to compositions and methods where a glucagon-like peptide affects appetite suppression in humans, especially in humans with diabetes.

BACKGROUND OF THE INVENTION

The physiological mechanisms that produce satiety after food intake have not yet been defined. Several peptides normally secreted from the gastrointestinal tract during eating have been shown to suppress food intake if given before meals (Smith, G. P. and J. Gibbs. In: Martin J B, et al. cds. *Neurosecretion and brain peptides*. New York: Raven, 389–395 (1981): Gibbs J. and Smith G. P. Fed. Proc. 45:1391–1395 (1986); Gibbs J. and Smith G. P. *Ann. N.Y. Acad. Sci.* 547:210–216 (1988)). During recent years, the role of the preabsorptive release of gut peptides (especially cholecystokinin, bombesin-like peptides and glucagon-like peptides) in the production of meal-ending satiety has been extensively investigated in animals (Gibbs J. and Smith G. P. (1988): Gibbs J. et al. *J. Comp. Physiol. Psychol.* 84:488–495 (1973); Bado A. et al., *Pharmacol. Biochem. Behav.* 31:297–303 (1988); Weller A. et al. *Science,* 247:1589–1591 (1989); Silver A. J. et al., *Am. J. Physiol.,* 256:R646 R652 (1989); Turton M. D. et al., *Nature* 379:69–72, (1996)). Cholecystokinin (CCK) and bombesin-like peptides have also been studied in humans (Lieverse R. J. et al., *Gastroenterology* 106: 1451–1454 (1994); Gutzwiller J. P. et al., *Gastroenterology* 106: 1168–1173 (1994)). CCK, the first gut peptide proposed to act as a satiety signal (Gutzwiller, J. P. (1994)), has received the major share of interest in human studies reported in the literature.

Glucagon-like peptide-1 (7–36) amide (GLP-1), the biologically active form of the GLP-1 protein resulting from a post-translational modification of the prohormone proglucagon, is released from enteroendocrine cells from the distal gut in response to food intake. GLP-1 has been shown to reduce food intake in rats when administered intracerebroventricularly, whereas intraperitoneal application of the peptide did not have any effect (Turton M. D. et al., *Nature* 379:69–72, (1996)). Further, when a GLP-1 receptor-specific antagonist was infused intracerebroventricularly, it blocked endogenous peptide, and thus affected only physiologically active circuits. Blocking endogenous GLP-1 causes healthy, already satiated animals to eat more. Turton and co-workers have, therefore, suggested that intracerebroventicular GLP-1 inhibits feeding in fasted rats (Turton, et al. (1996)). Others have reported no effect on appetite from the infusion of GLP-1 over 210 minutes in obese humans, thereby having discouraged further investigation of GLP-1 in human appetite suppression. These inconsistent studies have discouraged further investigation of GLP-1 for humans.

In animals, expression of GLP-1 receptors has been found in the hypothalamus, the brainstem and in the periventricular area, but not in the cortex. GLP-1 receptors were found in the endocrine pancreas (Hörsch. D. et al. *Pancreas* 14(3): 290–294 (1997)), the adipose tissue (Valverde I. et al., *Endocrinology* 132:75–79 (1993)) and the stomach (Uttenthal, L. O. and Blazquez, E. *FEBS Lett;* 262:139–141 (1990); Schmidtler J. et al.,*Am. J. Physiol.* 267:G423–G432 (1994)); and nerves containing GLP-1 have been identified in the brain (Jine S. L. C. et al., *J. Comp. Neurol.* 271: 519–532 (1988): Salazar I. and Vaillant C. *Cell Tissue Res.* 261:355–358 (1990)). Thus, the GLP-1 receptor is present at sites where administration of exogenous GLP-1 appears to cause satiety; however, whether it is a satiety factor has not been confirmed. Injection of GLP-1 into the cerebral ventricles of fasted rats inhibited feeding, and this effect was blocked by the GLP-1 receptor antagonist exendin (9–39). Also, administration of exendin (9–39) alone doubled food intake in satiated rats (Turton M. D. et al., *Nature* 379: 69–72, (1996)).

Even though GLP-1, as demonstrated here, controls appetite in normal humans, the use of GLP-1 to control appetite in diabetics is surprising for several reasons: first, diabetics normally have hypoinsulinemia, which is a major appetite stimulant. Accordingly, there would be an expected major uncertainty whether GLP-1 could counteract this stimulation and deliver appetite control. Secondly, diabetics are characterized by having hyperglycemia, which in many causes a functional deterioration of the autonomous neural control systems for the GI tract, and in later stages causes structural damage to these systems. Accordingly, there would be an expected major uncertainty whether GLP-1 could have an appetite control function in such diabetics.

It is a primary objective of the present invention to suppress human appetite with GLP-1 or its biologically active analogues.

Another objective of the present invention is to combine GLP-1 or its biologically active analogues with a pharmaceutically acceptable carrier to provide an effective treatment composition for humans for use in appetite control, including in diabetics.

A yet further objective of the present invention is to provide a method, means and composition userful by humans to reduce the spontaneous urge for food intake without significant adverse side effect consequences to the person's metabolic balance.

The method and manner of accomplishing each of the above objectives, as well as others, will be apparent from the detailed description of the invention which follows.

SUMMARY OF THE INVENTION

A composition comprising a compound which binds to a receptor for glucagon-like peptide-1, said composition containing an amount of said compound effective to control appetite in a human in combination with a pharmaceutical carrier. Also provided is a method for controlling appetite in a human and for reducing spontaneous food intake by administering to the human a composition comprising a compound which binds to the receptor for glucagon-like peptide-1 and a pharmaceutical carrier, said composition containing an amount of said compound effective to control appetite in a human. It is especially userful in humans with diabetes.

BRIEF DESCRIPTION OF THE DRAWINGS

FIG. 2 is a graph of subjective sensations of hunger (see Example 1) (FIG. 2A) and fullness (FIG. 2B) experienced by healthy male subjects before and after food intake during intravenous infusion of 5% glucose or one dose at various dose levels of human GLP-1.

FIG. 4 is a graph of plasma CCK levels (pmol/l) (FIG. 4A) and insulinogenic index (insulin/glucose) (FIG. 4B) in response to graded doses of GLP-1 (see Example 1).

DETAILED DESCRIPTION OF THE INVENTION AND ITS PREFERRED EMBODIMENTS

The inventors have discovered that the administration of graded doses of human GLP-1 produced plasma glucagon-like peptide-1 concentrations within physiological ranges and resulted in the reduction of intake of food in non-obese, healthy male subjects. Accordingly, the composition of the present invention is useful in therapeutic treatment for reducing food consumption.

The present invention provides a composition comprising a compound which binds to a receptor for glucagon-like peptide-1 which is effective to control appetite and spontaneous food uptake in humans. In one embodiment, the receptor-binding compound is glucagon-like peptide-1. In another embodiment, the receptor-binding compound is a variant peptide in which the combination of the substitutions, deletions and variants does not differ by more than five amino acids from glucagon-like peptide-1. The receptor-binding compound can further comprise a polynucleotide, or an organic molecule having a molecular weight of not greater than about 5000.

The term glucagon-like peptide-1 includes glucagon-like peptide-1 related peptides and peptides which result from natural or synthetic enzymatic or chemical processing of glucagon-like peptide-1 related peptides. These peptides include peptides derived from enzymatic or chemical processing of GLP-1 (1–37), GLP-1 (7–37) and GLP-1 (7–36) amide. Preferably, the composition comprises a receptor-binding compound selected from the group consisting of a peptide which comprises the amino acid sequence of glucagon-like peptide-1 described above, or a variant peptide comprising an amino acid sequence that varies from the sequence thereof by one or more substitutions, deletions or insertions. In one embodiment, the receptor-binding compound is glucagon-like peptide-1. In another embodiment, the receptor-binding compound is a variant peptide in which the combination of the substitutions, deletions and variants does not differ by more than five amino acids from glucagon-like peptide-1. The receptor-binding compound can also be a polynucleotide or an organic molecule having a molecular weight of not greater than about 5000. In this method, the composition preferably comprises a receptor-binding compound selected from the group consisting of a peptide comprising the amino acid sequence of glucagon-like peptide-1, which includes GLP-1 (7–37) and GLP-1 (7–36) amide, and a variant peptide comprising an amino acid sequence that varies from the sequence thereof by one or more substitutions, deletions or insertions. The preferred embodiments described for the composition are applicable to the method. In this aspect, the step of administering is preferably selected from the group consisting of a regimen of multiple subcutaneous injections, micropressure injection system, ambulatory pump, depot sustained-release injection, implant, deep lung sustained-release insufflation, skin patch, buccal patch or a sustained-release oral delivery dose form. Further, the step of administering preferably comprises providing graded dose regimen of doses in the range of from about 0.5 to about 2.0 pmol/kg per minute for intravenous delivery and to about 1–10 pmol/kg per minute for subcutaneous continuous delivery.

The inventors have demonstrated herein that short-term satiety effects can be induced by peripherally infused GLP-1. The results suggest that GLP-1 can act as an endogenous signal involved in the control of food intake in man.

The present composition can comprise glucagon-like peptides and related peptides and biologically active analogs of glucagon-like peptide-1 that bind to a glucagon-like peptide-1 receptor protein. The GLP-1 receptors are cell-surface proteins particularly including those present on insulin-producing beta cells. Glucagon-like peptides and analogs can include species that have insulinotropic activity and are agonists of, i.e., activate, the GLP-1 receptor molecule and its second messenger activity on inter alia insulin producing beta cells. Such agonists of glucagon-like peptide that exhibit activity through this receptor have been described: EP 0708179A2; Hjorth, S. A. et al. *J. Biol. Chem.* 269, (48):30121–30124 (1994); Siegel, E. G. et al. Amer. Diabetes Assoc. 57th Scientific Sessions, Boston (1997); Hareter, A. et al. Amer. Diabetes Assoc. 57th Scientific Sessions, Boston (1997); Adelhorst, K. et al. *J. Biol. Chem.* 269 (9):6275–6278 (1994); Deacon, C. F. et al. 16th International Diabetes Federation Congress Abstracts, *Diabetologia Supplement* (1997), Irwin. D. M. et al., *Proc. Natl. Acad. Sci. USA.* 94:7915–7920 (1997); Mosjov, S. *Int. J. Peptide Protein Res.* 40:333–343 (1992). Polynucleotides also include numerous species that are agonists of, i.e., activate, the GLP-1 receptor molecule and its second messenger activity on inter alia insulin producing beta cells, and include exendin-4 (see WO97/46584). GLP-1 mimetics that also are agonists of beta cells include, for example, enkephalin motif compounds. Glucagon-like peptide-1 antagonists are also know, for example see e.g. Watanabe, Y. et al., *J. Endocrinol.* 140(1):45–52 (1994), and include exendin (9–39) amine an exendin analog, which is a potent antagonist of GLP-1 receptors (see. e.g. WO97/46584).

Further embodiments include such proteins that are chemically synthesized, as well as any proteins or fragments thereof that are substantially homologous. "Substantially homologous", which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

It goes without saying that certain modifications to GLP-1 itself, or to the composition containing the same, may be made without departing from the spirit or scope of the present invention, and these are meant by the term biologically active analogues. Put another way, modifications both in the formula to provide some related analogues of GLP-1, and in the composition to provide either other forms of administration, or other pharmaceutically-acceptable related compositions, may be made, as long as the desired human appetite control is achieved. These modifications are included in the scope of this invention.

Mammalian GLP peptides and glucagon are encoded by the same gene. In the ileum the phenotype is processed into two major classes of GLP peptide hormones, namely GLP-1 and GLP-2. There are four GLP-1 related peptides known which are processed from the phenotypic peptides. GLP-1 (1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated by post translational processing to yield GLP-1 (1–36) NH, which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) SEQ ID NO:2; or is enzymatically processed to yield GLP-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1 (7–37) can also be amidated to yield GLP-1 (7–36) amide which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:4).

Intestinal L cells secrete GLP-1 (7–37) (SEQ ID NO:3) and GLP-1 (7–36) NH$_2$ (SEQ ID NO:4) in a ratio of 1 to 5 respectively. These truncated forms of GLP-1 in situ have short half-lives, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5); and Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:6), respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg.

(NH$_2$) (SEQ ID NO:6), have been speculated to affect hepatic glucose production, but do not stimulate the production or release of insulin from the pancreas.

There are six peptides in Hela monster venoms that are homologous to GLP-1
a=GLP-1 SEQ ID NO:4
b=Exendin 3 SEQ ID NO:7
c=Exendin 3(9–39)NH$_2$ SEQ ID NO:8
d=Exendin 4 SEQ ID NO:9
e=Helospectrin I SEQ ID NO:10
f=Helospectrin II SEQ ID NO:11
g=Helodermin SEQ ID NO:12
h=Q$^8$, Q$^9$ Helodermin SEQ ID NO:13

The major homologies as indicated by the outlined areas in the Table are: peptides c and h are derived form b and g respectively. All 6 naturally occurring peptides (a, b, d, e, f and g) are homologous in positions 1, 7, 11 and 18. GLP-1 and exendins 3 and 4 (a, b and d) are further homologous in positions 4, 5, 6, 8, 9, 15, 22, 23, 25, 26 and 29. In position 2. A. S and G are structurally similar. In position 3, residues D arid E (Asp and Glu) are structurally similar. In positions 22 and 23 F (Phe) and I (Ile) are structurally similar to Y (Tyr) and L (Lcu), respectively. Likewise, in position 26, L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 like proteins or peptides can be made by solid state direct amino acid synthesis. GLP-1 can also be made by conventional recombinant techniques described in detail for example in Sambrook and Maniaitis. "Recombinant", as used herein, means that a protein is derived from recombinant (e.g., microbial or mammalian) expression systems.

The GLP-1 like proteins or peptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. High performance liquid chromatography (HPLC) can be employed for final purification steps.

The polypeptides of the present invention may be a naturally purified product, or a product of chemical synthetic procedures, or produced by recombinant techniques from prokaryotic or cukaryotic hosts (for example by bacterial, yeast, higher plant, insect and mammalian cells in culture). Depending on the host employed in a recombinant production procedure, the polypeptides of the present invention may be glycosylated or may be non-glycosylated. Polypeptides of the invention may also include an initial methionine amino acid residue.

GLP-1 activity can be determined by standard methods, in general, by receptor-binding activity screening procedures involve providing appropriate cells which express the receptor on the surface thereof, for example insulinoma cell lines such as RINmSF cells or INS-1 cells. See also Mosjov, S. (1992) and EP0708170A2. In addition to measuring specific binding of tracer to membrane, cAMP activity or glucose dependent insulin production can also be measured. In one method, a polynucleotide encoding the receptor of the present invention is employed to transfect cells to thereby express the GLP-1 receptor protein. Thus, for example, such assay may be employed for screening for a receptor agonist by contacting such cells with compounds to be screened and determining whether such compounds generate a signal, i.e. activate the receptor.

Other screening techniques include the use of cells which express the GLP-1 protein receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

The glucagon-like peptide-1 receptor binding proteins of the present invention may be used in combination with a suitable pharmaceutical carrier for an appetite control therapeutic. Such compositions comprise a therapeutically effective appetite suppression control amount of the polypeptide, and a pharmaceutically acceptable carrier or excipient. Such a carrier includes, but is not limited to, saline, buffered saline, dextrose, water, glycerol, ethanol, lactose, phosphate, mannitol, arginine, trehalose and combinations thereof. The formulations should be pharmaceutically elegant and suit the mode of administration. Although not limited to the following ranges and provided as an illustration, suggested dose ranges for various applications are 0.1 to $5.0 \times 10^{-12}$ mol/kg min for intravenous administration; 0.1 to 5.0 nmol/kg GLP-1 in any form as a single subcutaneous shot; continuous subcutaneous administration in a range from about 0.2 to $20 \times 10^{-12}$ mol/kg min. It is believed that the subcutaneous amounts may be up to or at least 10 times higher than those for intravenous application.

EXAMPLES

The following examples further illustrate an aspect of the present invention. However, it is in no way a limitation of the teachings or disclosure of the present invention as set forth herein.

Example 1 and FIGS. 1–5

The Effect of Graded Intravenous Doses of Synthetic Human GLP-1 on Food Intake in Healthy Male Volunteers A randomized, double-blind design was carried out with 16 healthy men aged 23.6±0.5 years. The weight of all subjects was within normal range considering their age, sex, and height. Each subject gave written informed consent for the study.

Four treatments (0, 0.375, 0.75 and 1.5 pmol/kg), separated by at least 7 days, were administered to the 16 subjects. The treatments were identical in design (FIG. 1), except for the intravenous infusion of 5% glucose as placebo control or one dose of GLP-1. An identical standard meal was presented to the subjects on each occasion. The meal consisted of orange juice as an appetizer (480 kcal per 1); ham sandwiches (60 g bread, 10 g butter, 25 g ham 266 kcal per sandwich) and more orange juice and chocolate pudding (172 kcal per 100 g): coffee with cream and sugar (coffee could be sweetened if desired; therefore both cream and sugar were optional @ 12 g cream=20 kcal, 4.5 sugar=18 kcal). No other food or liquid was allowed during the study. At the end of the study, the amount of food eaten and the amount of fluid ingested was measured by absolute weight from which total caloric intake (food and fluid intake) was calculated.

Each subject was free to eat and drink as much as he wished, but the order of food intake had to follow the above schedule. To reduce participant's awareness of the amount of food being provided, food was served in excess.

On the first day of each treatment, each subject ate breakfast, if this was his normal custom; however, no snacks were allowed after 8:00 a.m. At 12:00 noon, an intravenous infusion of glucose 5%, or one dose of synthetic GLP-1 (7–36) amide at 0, 0.375, 0.75 and 1.5 pmol/kg per min, dissolved in 5% glucose solution was started in each subject and continued for the duration of each treatment. Infusions were delivered by ambulatory infusion pumps through a teflon catheter inserted into a forearm vein. Participants were able to sit, eat, stand and walk comfortably while receiving infusions. At 60 minutes after the start of the respective infusion, the test meal was presented and each participant was invited to eat and drink as much as he liked.

Beginning at 12:00 noon, the subjects scored their subjective feelings of hunger and fullness at 15 minute intervals throughout the treatments using a visual analogue scale of 0–10 and indicated the scores on a questionnaire. The scales and scores were designed as previously described (Welch I. M. et al. *Gut* 29:306–311 (1988); Welch I. M. et al. *Gastroenterology* 89:1293–1297 (1985); Drewe, J. et al. *Gastroenterology* 102:1654–1659 (1982)). For example, a score of 0 for hunger indicated the subject was not hungry at all, 2 indicated slightly hungry, 5 indicated moderately hungry, 8 indicated very hungry, and 10 indicated absolutely ravenous.

The quantity of food eaten and volume of fluid drunk was measured. The time for each subject to complete his meal was also measured. From these observations, the average rate of food and fluid intake, as well as the calorie intake, could be calculated. In the pre-meal period and after eating, blood was drawn at regular intervals into ethylenediaminetetraacetic acid (EDTA) tubes containing aprotinine (1000 KIU/ml blood) for glucose and hormone determinations.

The GLP-1 infusions were prepared from a freeze-dried synthetic powder, GLP-1 (7–36) amide purchased from Bachem (Bubendorf, Switzerland). The peptide was dissolved in 0.9% saline containing 0.5% human serum albumin, and prepared under aseptic conditions. Aliquots of 50 μg/5 ml were stored at $-20°$ C. Infusion solutions were prepared by diluting appropriate amounts of GLP-1 with 5% glucose containing 0.1% human serum albumin. Control solutions contained albumin in 5% glucose alone; and were indistinguishable in appearance from GLP-1 infusions. Treatments were delivered in a double-blind fashion.

Figure 1:
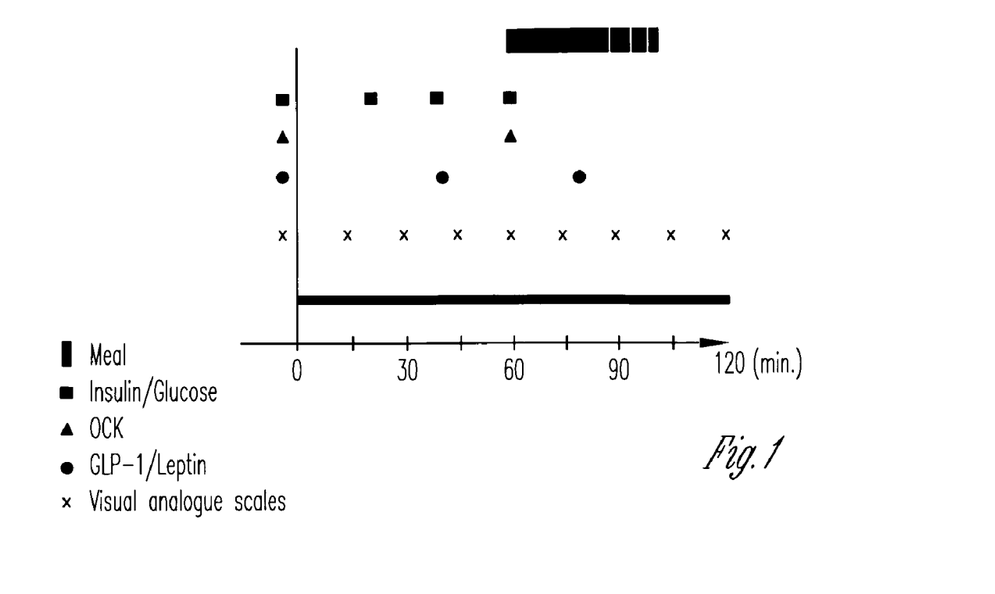
FIG. 1 is a graph of daily time course of procedures (see Example 1) carried out in a randomized, double-blind study with 16 healthy men aged 23.6 ±−/5 years/Dosage treatments of 0.375, 0.75 and 1.5 pmol/kg of GLP-1, separated by at least 7 days, were administered to the 16 subjects for 120 minutes with an intravenous infusion of 5% glucose used as a placebo control.

Glucose concentrations were measured by the hexokinase method. Plasma hormone concentrations of insulin, cholecystokinin, GLP-1 and leptin were measured as depicted in FIG. 1. All hormone concentrations were determined by specific radioimmunoassay systems. For insulin and leptin concentrations commercially available test kits were used. Plasma immunoreactive CCK concentrations were measured by a sensitive radioimmunoassay based on the antiserum OAL656 which recognizes the sulfated tyrosine residue of CCK8, but has no relevant cross-reactivity with sulfated gastrin (<1%) and does not cross-react with unrelated gastrointestinal peptides (Hashimura, E. et al., *J. Immunol. Methods* 55:375–387 (1982)). GLP-1 was measured as previously described (Schirra, J. et al. Proc. Assoc. Am. Phys. 109(1):84–971 (1997)). The detection limit of the GLP-1 assay was 2 fmol/tube. The assay does not have any significant cross-reactivity with GIP, pancreatic glucagon, glicentin, oxyntomodulin or GLP-2. Intra-assay and inter-assay coefficients of variation were 3.4% and 10.4%, respectively.

The amount of food eaten and the amount of fluid drunk, the corresponding energy intake, and the duration of meal consumption were compared between the four by one-way analysis of variance (ANOVA) using the general linear model (GLM) procedure of the SAS software package (SAS Release 6.03. Cary, N C: SAS Institute, 1988). In the event of significant differences, ANOVA was followed by the Newman-Keuls multi-comparison test for pairwise comparisons (Sachs, L. Angewandte Statistik. Berlin, Springer, (1984)). The same statistical procedure was used to analyze the results of GLP-1 induced changes in plasma hormone concentrations using area under the curve (AUC) analysis. Scores for hunger and fullness were compared at the different time points before and after meals between the different treatments using multiple paired t-tests with Bonferroni correction (Sachs, L. Angewandte Statistik. Berlin, Springer, (1984)).

Intravenous infusion of graded doses of synthetic human GLP-1 dose-dependently reduced the amount of food eaten and the amount of fluid consumed ($p<0.001$ and $p<0.01$ respectively, Table 2). A maximal reduction of 35% in food consumption occurred with the highest dose of GLP-1 (1.5 pmol/kg per hour), resulting in a decrease in calorie intake of 32% ($p<0.001$: Table 2).

TABLE 2

(Effect of graded doses of human GLP-1 on eating behaviour in 16 healthy male subjects)

| Treatment | Control | GLP-1 0.375 (pmol/kg/min) | GLP-1 0.75 (pmol/kg/min) | GLP-1 1.5 (pmol/kg/min) |
|---|---|---|---|---|
| Food quantity | 587 ± 36 | 531 ± 35* | 516 ± 40* | 384 ± 34*** |
| Calorie intake (kcal) | 1627 ± 97 | 1520 ± 95 | 1451 ± 101* | 1107 ± 84*** |
| Meal duration (min) | 38 ± 3 | 35 ± 3 | 34 ± 3* | 30 ± 3* |
| Fluid intake (ml) | 708 ± 57 | 748 ± 52 | 689 ± 48* | 584 ± 45** |

(data are mean 4 SEM).
$p < 0.05$ vs control
**$p < 0.01$ vs control
***$p < 0.001$ vs control Meal duration for subjects during GLP-1 infusions was also dose-dependently decreased compared to subjects infused with placebo and reached statistical significance at the highest dose ($p<0.05$). None of the participants reported any abdominal discomfort or side effects during any infusions. Furthermore, when questioned at the end of each experiment, none of the participants experienced or reported any adverse reactions.

Figure 2A:
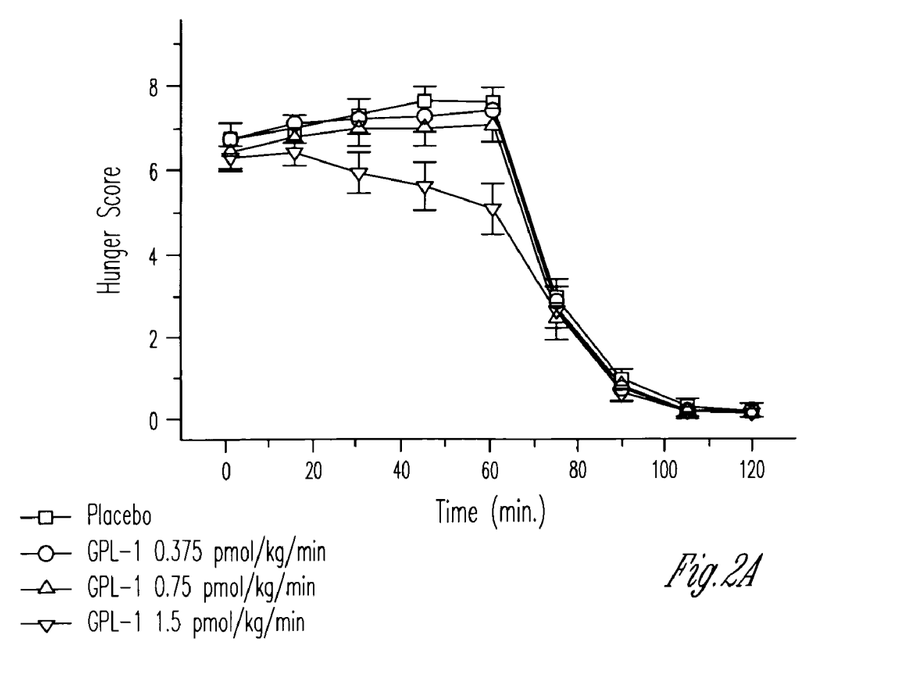
Figure 2B:
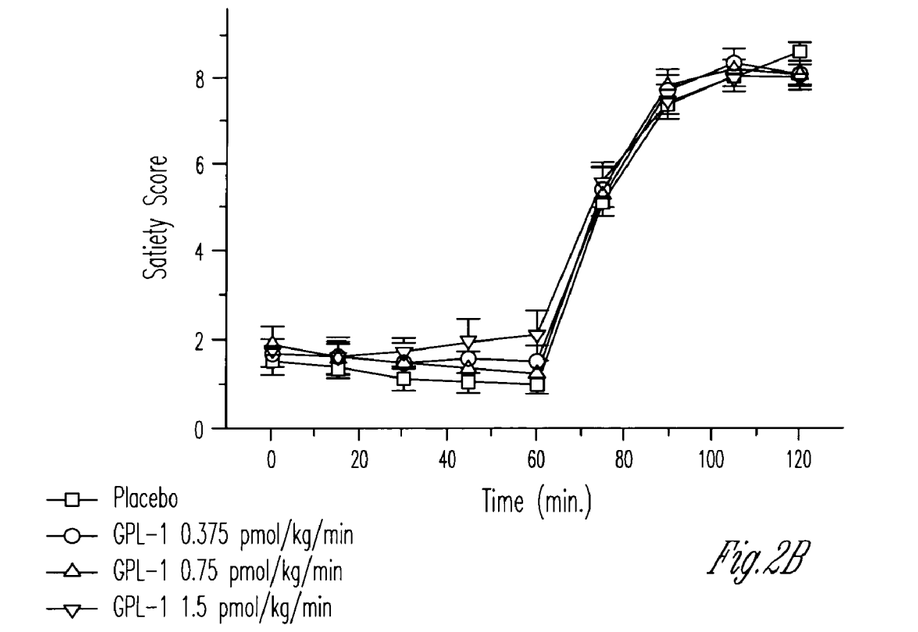

The subjects experienced a reduced degree of hunger and a concomitant feeling of fullness in the pre-meal period with infusions of increasing doses of GLP-1. The difference reached statistical significance only for the highest dose of GLP-1 with respect to hunger and fullness feelings ($p<0.05$–$0.01$, FIG. 2). No statistical differences were observed thereafter in hunger or fullness scores with any treatment after meal intake.

Figure 3:
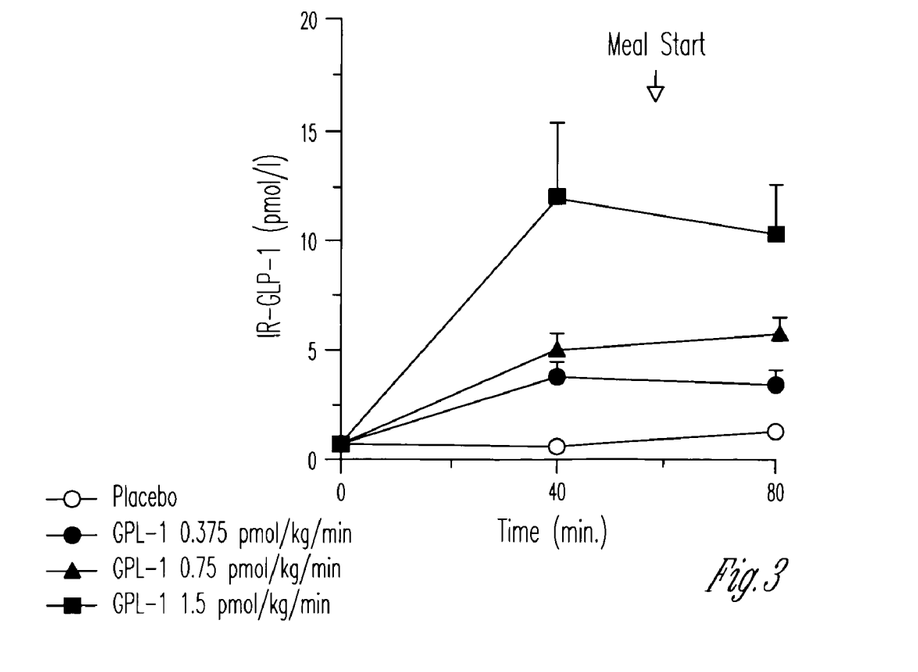
FIG. 3 is a graph of immunoreactive GLP-1 (IR-GLP-1) measured in the plasma (pmol/1) in response to graded doses of intravenous GLP-1 (see Example 1).

Graded doses of exogenous GLP-1 produced dose-dependent increases in plasma GLP-1 concentrations (FIG. 3). The lower two doses produced plasma levels of 3.7±0.6 pmol/l and 5.0±0.6 pmol/l, respectively, which can be considered physiological postprandial plasma levels, whereas the highest dose of GLP-1 resulted in supraphysiological plasma concentrations (Byrne, M. M. and Göke, B. Diabetes. Basel. Karger (13):219–233 (1997).

In the control experiment, glucose levels and insulin concentrations remained at pre-meal period levels. GLP-1 induced a dose-dependent, short-lasting increase in blood glucose and plasma insulin concentrations. The results are depicted as an insulinogenic index in FIG. 4. The insulinogenic index, calculated as the quotient insulin/glucose, more appropriately reflects insulin release (Schirra, J. et al. *Proc. Assoc. Am. Phys.* 109 (1):84–9 (1997)) than changes of plasma glucose which invariably are associated with changes in plasma insulin.

Figure 4A:
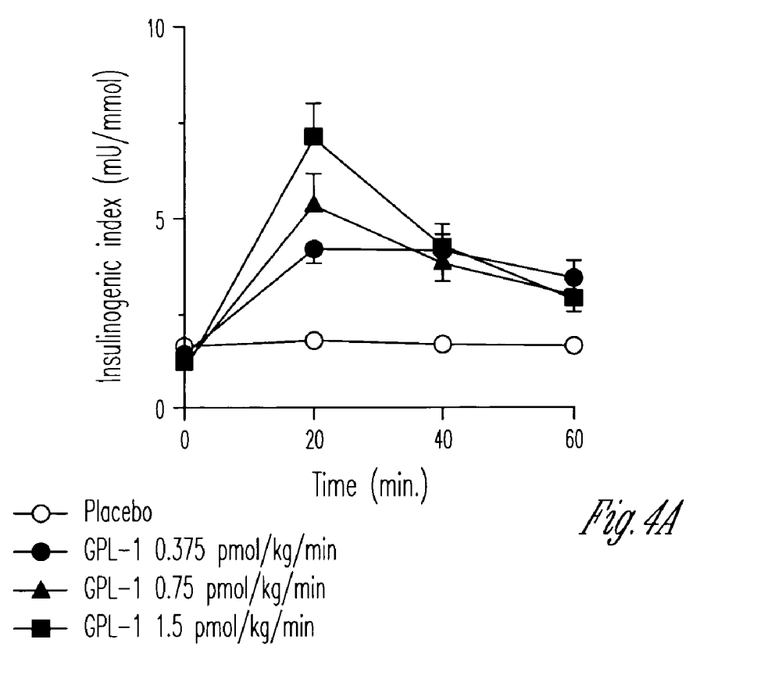
Figure 4B:
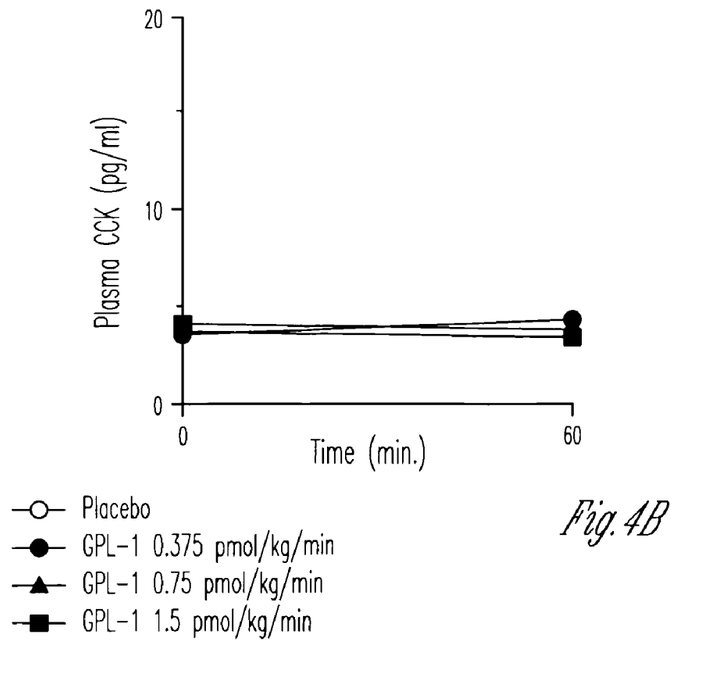

Plasma CCK concentrations did not change in the pre-meal period with any dose of GLP-1 (FIG. 4). The results presented demonstrate that CCK is not released after graded doses of GLP-1 in the pre-meal period making it unlikely that CCK is the mediator of this response.

Figure 5:
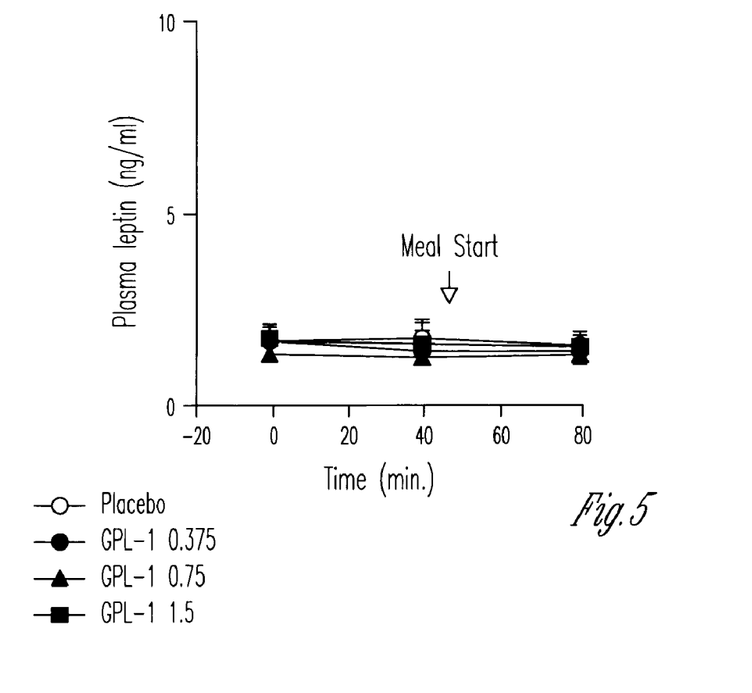
FIG. 5 is a graph of plasma leptin concentrations (ng/ml) in response to graded doses of intravenous GLP-1 (see Example 1).

Finally, leptin levels did not change with any dose of GLP-1 administered, nor did leptin levels increase after meal intake (see FIG. 5). Leptin, the product of the adipose-specific ob gene, regulates food intake and energy expenditure in animals (Campfield, L. A., et al. *Science* 269: 546–549 (1995); Halaas, J. L. et al. *Science* 269:543–546 (1995); Pellymounter, M. A. et al. *Science* 269:540–543 (1995)). An effect of leptin influencing short-term satiety has not yet been demonstrated in humans, but an action of postprandial increase of GLP-1 stimulating adipose tissue to secrete leptin and suppress food intake is proposed. Leptin plasma concentrations did not change even during a pharmacological GLP-1 infusion (FIG. 5) thus confirming results of Shalev et al. (Shalev, A. et al. *Metabolisrn* 46 (7):723–725 (1997)). The latter finding indicates that food intake suppression induced by GLP-1 is not mediated by leptin.

Graded GLP-1 infusions resulted in a dose-dependent reduction in food intake (maximal inhibition 35%; $p<0.001$ vs control) and a similar reduction in calorie intake (32%; $p<0.001$). Fluid ingestion was also reduced by GLP-1 (18% reduction, $p<0.01$). There were no overt side effects produced by GLP-1, but subjects experienced less hunger and early fullness in the pre-meal period during GLP-1 infusion at the highest dose ($p<0.05$).

These results demonstrate that intravenous infusions of GLP-1 decrease spontaneous food intake even at physiological plasma concentrations. The date suggest an important role for GLP-1 in the regulation of the early satiety response in humans.

Example 2

Twelve male patients were recruited for the study who had diabetes mellitus type 2 for at least one year. Patients were admitted to a Research Unit after given written informed consent and after the experimental protocol had been explained to them. The mean age of the patients was 55±2 years; their mean $HbA_1C$ was 8.1±4 and their mean BMi was 29.4±1.2. Seven patients were on oral antidiabetics. The participants were tested on two different days in a placebo-controlled, randomized, double-blind, crossover study. The two test days were separated by at least one week and by no more than three weeks.

On each test day, patients arrived in the Research Unit in the morning, having fasted overnight. A standardized, fixed energy breakfast was then served and it had to be completed before 8:30 a.m. After breakfast, patients were able to read and listen to music. At 11:00 a.m., two venflon catheters were inserted into the anticubital veins of each arm, one for infusion, the other one for blood drawing. At 11:30 a.m. a fasting blood sample was taken and infusion was started (either GLP-1 at a dose of 1.5 pmol/kg per min or saline as placebo) and continued for the next two hours. Infusions were delivered by ambulatory infusion pumps. 60 min after the start of the respective infusion, a test meal was presented and the participants were invited to eat and drink as much as they liked.

Beginning with the infusions, participants scored their subjective feelings of hunger and fullness in 15 min intervals throughout the experiments using visual analogue scales (VAS) of 0–10 with text expressing the most positive and most negative rating anchored at each end. VAS were used to assess hunger, fullness, and prospective food consumption using scales and scores which have previously been designed.

Each subject was free to eat and drink as much as he wished until "comfortably satisfied" of a standard meal which consisted of a) orange juice as an appetizer (480 kcal/l); b) ham sandwiches (60 g, 10 g butter, 25 g ham: 266 kcal/sandwich) with more orange juice or with water; c) strawberry mousse (100 kcal/100 g); d) coffee with cream (coffee could be sweetened with aspartam if desired; both cream and aspartam were optional; 12 g cream=20 kcal). No additional food or fluid was allowed during the study. In addition, the order of food intake had to follow the above schedule. To reduce participants' awareness of the amount of food being provided, food was served in excess. The quantity of food eaten and the quantity of fluid drunk were measured. From these observations, the total energy intake could be calculated. In the pre-meal period and after eating, blood samples were taken in regular intervals for glucose and hormone determinations. Adverse events were assessed by the attending physician through close observation of each patient; in addition, each participant was questioned after each experiment and after he had completed the two tests whether he had experienced any adverse events.

For the GLP-1 infusions, commercially available synthetic human GLP-1 (7–36) amide was purchased form Bachem, Bubendorf, Switzerland. The peptide was dissolved in 0.9% saline solution containing 0.5% human serum albumin and prepared under aseptic conditions by the University of Basel Hospital Pharmacy. Aliquots of 50 $\mu$g/5 ml were stored at –20° C. Infusion solutions were prepared by diluting appropriate amounts of GLP-1 with 0.9% saline containing 0.1% human serum albumin. Control solutions contained albumin in 0.9% saline alone; they were indistinguishable in appearance from GLP-1 infusions. The solutions were prepared by a pharmacist who was not involved in the study. The physician in charge of the experiment was therefore not aware of the respective treatment, thereby making it possible to conduct treatments in a double-blind fashion.

Blood was drawn through the indwelling anticubital cannula into syringes on ice. These contained EDTA (6 $\mu$mol/l) and aprotinine (1000 KIU/l). After centrifugation, plasma hormone analyses were kept frozen at –20° C. Plasma glucose was analyzed by the glucose oxidase method. Insulin and glucagon concentrations in plasma were analyzed by commercially available radioimmunoassay kits (Biermann, Bad Nauheim, Germany). Immunoreactive GLP-1 was measured using the specific polyclonal antibody GA 1178 (Affinity Research, Nottingham, UK). Immunoreactivities were extracted from plasma samples on C-18 cartridges using acetonitrile for elution of samples. The detection limit of the assay was 0.25 pmol/l. Intra-and interassay coefficients of variation were 3.8% and 10.9%, respectively.

The amount of food eaten and the amount of fluid drunk as well as the corresponding energy intake were compared between the two treatments by Wilcoxon Signed Ranks Test using an SAS software package. The same statistical procedure was used to analyze the results of GLP-1-induced changes in plasma hormone concentrations using the Area Under the Curve (AUC) analysis. Scores for hunger and fullness were compared by calculating the S score from baseline (0 min) to 60 min of infusion using the Wilcoxon Signed Ranks Test. Differences were considered significant if p was <0.05.

Intravenous infusion of synthetic GLP-1 dramatically reduced the amount of food eaten and the amount of fluid consumption (p=0.034 and p=0.011 respectively; Table 3). The maximal reduction in food consumption with GLP-1 amounted to 29%, resulting in a decrease in calorie intake of 27% (p=0.034).

TABLE 3

(effect of GLP-1 (1.5 pmol/kg per min) on eating behaviour in 12 patients with diabetes mellitus type 2 compared with saline (control)).
Data are mean ± SEM.

| Parameter | Saline | GLP-1 |
|---|---|---|
| Food Quantity (g) | 377 ± 45 | 268 ± 31* |
| Calorie intake (kcal) | 944 ± 99 | 694 ± 79* |
| Fluid intake (ml) | 441 ± 58 | 360 ± 60** |

*) p = 0.034
**) p = 0.011

None of the participants reported any abdominal discomfort or side effects during any infusion of GLP-1. Furthermore, when questioned at the end of each experiment, none of them experienced or reported any adverse reaction.

Figure 6A:
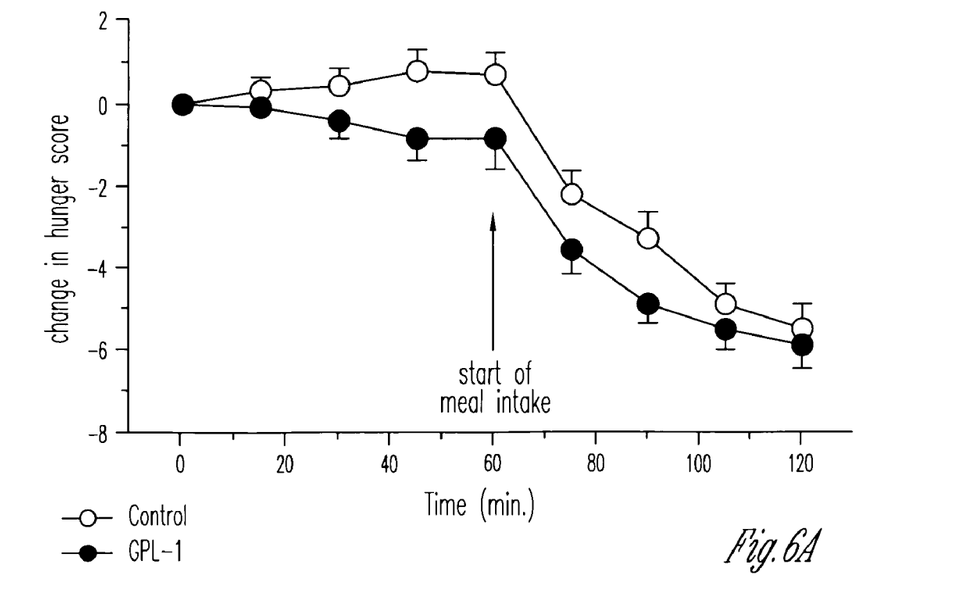
FIGS. 6(A) and (B) show appetite scores (hunger and fullness) for the twelve patients of Example 2.
Figure 6B:
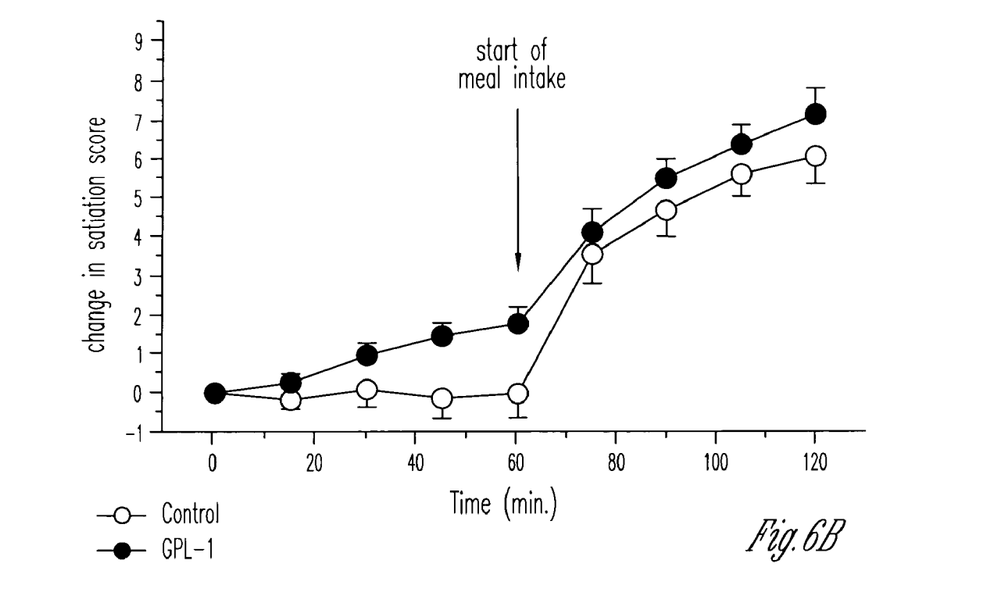
Figure 7A:
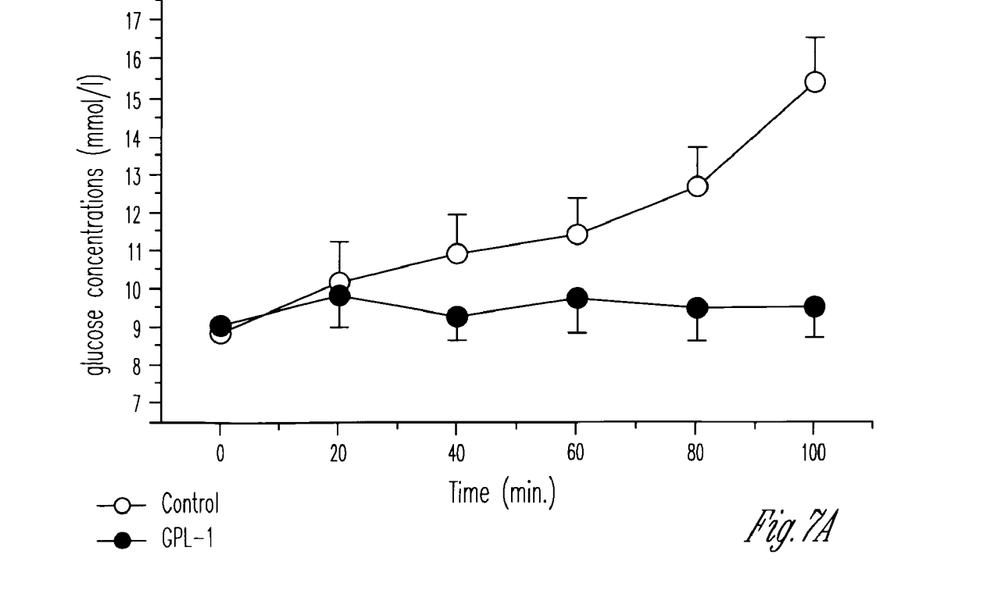
FIGS. 7(A)–(D) show the plasma glucose, plasma glucagon, and plasma GLP-1 concentrations, as well as insulinogenic index for the 12 patients of Example 2.
Figure 7B:
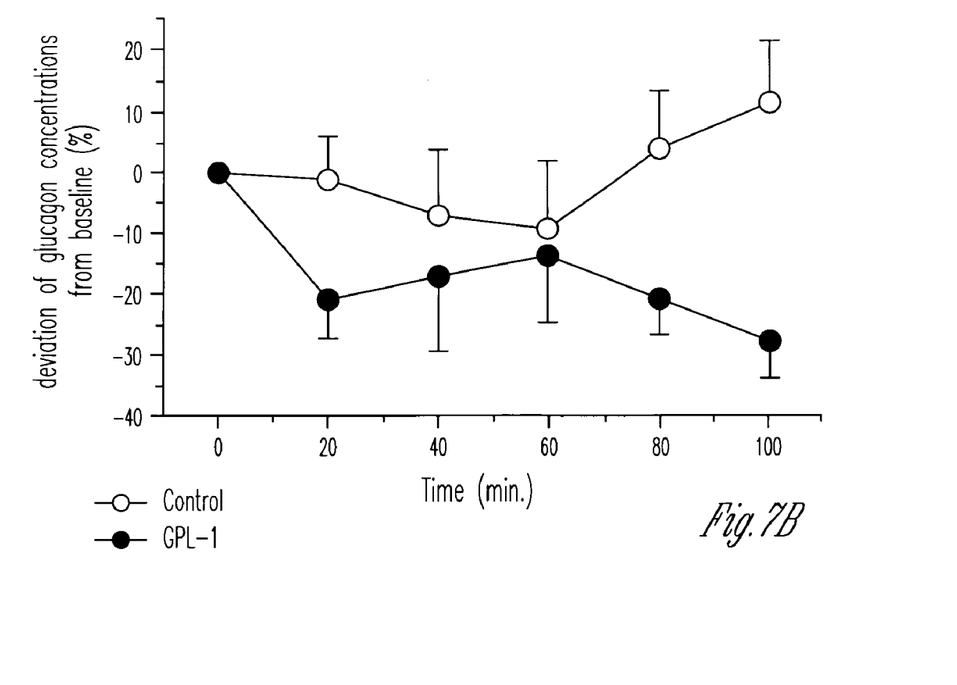
Figure 7C:
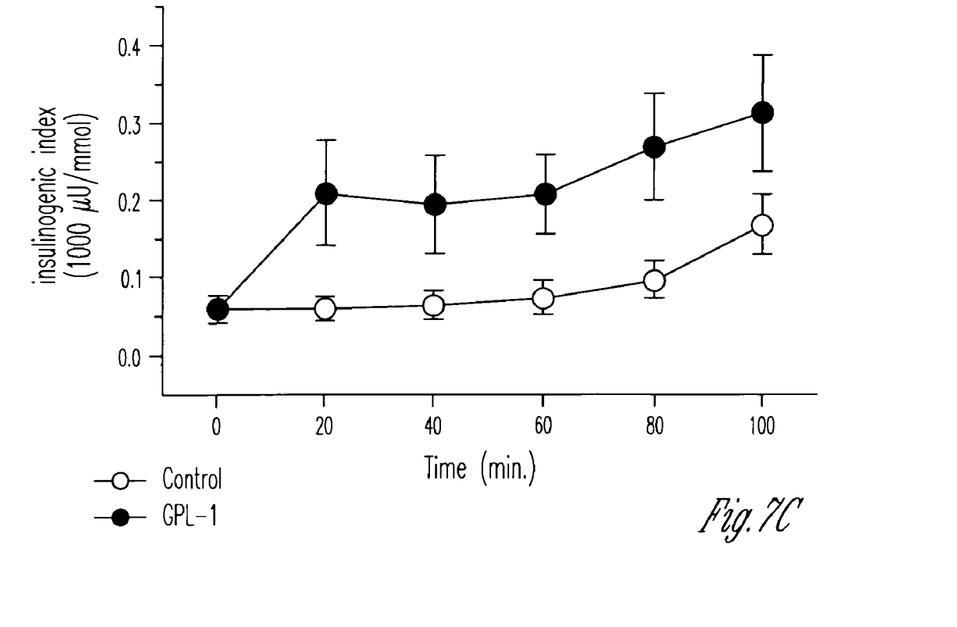
Figure 7D:
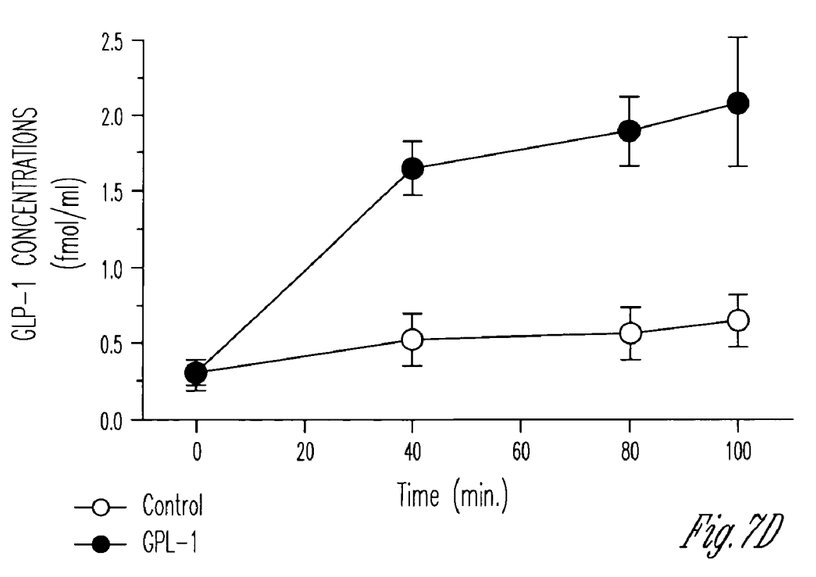

The GLP-1 infusion significantly influenced the mean VAS (FIG. 6). Subjects experienced a reduced degree of hunger and a concomitant increased feeling of fullness in the pre-meal period with GLP-1 infusion. When baseline scores were compared with the 60 min values, the difference reached statistical significance (p=0.028 for fullness and p=0.026 for hunger). Subjects felt less hungry and fuller with GLP-1 infusion compared with saline administration.

FIG. 7 shows blood glucose, plasma insulin, and glucagon levels. Pre-study blood glucose concentrations were slightly hyperglycemic, but similar in both experiments. There was a continuous increase in blood glucose in response to meal intake in the control experiment. With GLP-1, blood glucose levels were significantly (AUC=1197±101 mmol×min/L with saline vs 765±65 with GLP-1; p<0.0001) lower for the duration of the experiment (FIG. 7). Insulin concentrations were significantly (AUC=1775±357 $\mu$U×min/L for saline vs 2920±516 with GLP-1; p<0.0001) increased with GLP-1 compared to saline infusion, whereas the glucagon response was significantly reduced (p<0.006) with GLP-1. The GLP-1 infusion increased the plasma concentrations of GLP-1 (FIG. 7).

Example 2 demonstrates that peripherally administered GLP-1 significantly reduces energy intake by inhibiting hunger sensations in patients with diabetes mellitus type 2. The marked effect on appetite is clearly illustrated by each of the food parameters, and accompanied with lower fasting as well as meal-stimulated plasma glucose concentrations. These data extend previous findings (Examples) in healthy volunteers that exogenous GLP-1 acts as a physiological regulator of food intake and appetite sensations.

It therefore can be seen that the present invention accomplishes all of its stated objectives.

What is claimed is:

1. A method for controlling appetite in a human comprising: peripherally administering to a human a compound which binds to a receptor for glucagon-like peptide-1 and a pharmaceutical carrier, wherein said compound comprises GLP-1 (1–37), GLP-1 (7–37), GLP-1 (7–36) or a biologically active analog of GLP-1 (1–37), GLP-1 (7–37), GLP-1 (7–36) in an amount effective to control appetite in a human, wherein said biologically active analog of GLP-1 (1–37), GLP-1 (7–37), GLP-1 (7–36) contains one or more substitutions, deletions or insertions of not more than five amino acids from the amino acid sequence of GLP-1 (1–37), GLP-1 (7–37), or GLP-1 (7–36).

2. The method of claim 1 wherein the receptor-binding compound is glucagon-like peptide-1 (7–37) comprising the sequence His Ala Glu Gly Thr Phe Thr Ser Asp Val Ser Ser Tyr Leu Glu Gly Gln Ala Ala Lys Glu Phe His Ala Trp Leu Val Lys Gly Arg Gly (SEQ ID NO:3).

3. The method of claim 1 wherein the receptor-binding compound is glucagon-like peptide-1 (7–36) amide comprising the sequence His Ala Glu Gly Thr Phe Thr Ser Asp Val Ser Ser Tyr Leu Glu Gly Gln Ala Ala Lys Glu Phe His Ala Trp Leu Val Lys Gly Arg (NH$_2$) (SEQ ID NO:4).

4. The method of claim 1 wherein said administering comprises providing a graded dose regimen of doses in the range of from about 0.315 to about 2.0 pmol/kg per minute.

5. The method of claim 1 wherein said administering is in a manner selected from the group consisting of intravenous administration, single subcutaneous shot, continuous subcutaneous administration, a regimen of multiple subcutaneous injections, micropressure injection system, ambulatory pump, depot sustained-release injection, implant, deep lung sustained-release insufflation, skin patch, buccal patch and a sustained-release oral delivery dose form.

6. The method of claim 5 wherein said intravenous administration is in a dose range of from about 0.1 pmol to about 5.0 pmol/kg min.

7. The method of claim 5 wherein said single subcutaneous shot administration is in a dose range of from about 0.1 to about 5.0 nmol/kg.

8. The method of claim 5 wherein said continuous subcutaneous administration is in a dose range of from about 0.2 pmol to about 20 pmol/kg min.

9. A method for reducing food intake in a human comprising: peripherally administering to a human a compound which binds to the receptor for glucagon-like peptide-1 and a pharmaceutical carrier, wherein said compound comprises GLP-1 (1–37), GLP-1 (7–37), GLP-1 (7–36) or a biologically active analog of GLP-1 (1–37), GLP-1 (7–37), a human, wherein said biologically active analog of GLP-1 (1–37), GLP-1 (7–37), GLP-1(7–36) contains one or more substitutions, deletions or insertions of not more than five amino acids from the amino acid sequence of GLP-1 (1–37), GLP-1 (7–37), or GLP-1 (7–36).

10. The method of claim 9 wherein the receptor-binding compound is glucagon-like peptide-1 (7–37) comprising the sequence His Ala Glu Gly Thr Phe Thr Ser Asp Val Ser Ser Tyr Leu Glu Gly Gln Ala Ala Lys Glu Phe His Ala Trp Leu Val Lys Gly Arg Gly (SEQ ID NO:3).

11. The method of claim 9 wherein the receptor-binding compound is glucagon-like peptide-1 (7–36) amide comprising the sequence His Ala Glu Gly Thr Phe Thr Ser Asp Val Ser Ser Tyr Leu Glu Gly Gln Ala Ala Lys Glu Phe His Ala Trp Leu Val Lys Gly Arg (NH$_2$) (SEQ ID NO:4).

12. The method of claim 9 wherein said administering comprises providing a graded dose regimen of doses in the range of from about 0.1 to about 20 pmol/kg per minute.

13. The method of claim 9 wherein the compound is effective to reduce spontaneous food intake in a human.

14. The method of claim 9 wherein said administering is in a manner selected from the group consisting of intravenous administration, single subcutaneous shot, continuous subcutaneous administration, a regimen of multiple subcutaneous injections, micropressure injection system, ambulatory pump, depot sustained-release injection, implant, deep lung sustained-release insufflation, skin patch, buccal patch and a sustained-release oral delivery dose form.

15. The method of claim 14 wherein said intravenous administration is in a dose range of from about 0.1 pmol to about 5.0 pmol/kg min.

16. The method of claim 14 wherein said single subcutaneous shot administration is in a dose range of from about 0.1 to about 5.0 nmol/kg.

17. The method of claim 14 wherein said continuous subcutaneous administration is in a dose range of from about 1.0 pmol to about 10 pmol/kg min.

18. A method for controlling appetite in a human with diabetes comprising: peripherally administering to a human having diabetes a compound which binds to the receptor for glucagon-like peptide-1 and a pharmaceutical carrier, wherein said compound comprises GLP-1 (1–37), GLP-1 (7–37), GLP-1 (7–36) or a biologically active analog of GLP-1 (1–37), GLP-1 (7–37), GLP-1 (7–36) in an amount effective to control appetite in a human with diabetes, wherein said biologically active analog of GLP-1 (1–37), GLP-1 (7–37), GLP-1 (7–36) contains one or more substitutions, deletions or insertions of not more than five amino acids from the amino acid sequence of GLP-1 (1–37), GLP-1 (7–37), or GLP-1 (7–36).

19. A composition for suppressing appetite in a human comprising: a compound prepared for intravenous administration in a dose range of from about 0.1 pmol to about 5.0 pmol/kg min which binds to a receptor for glucagon-like peptide-1, and a pharmaceutical carrier, wherein said compound comprises GLP-1(1–37), GLP-1 (7–37), GLP-1 (7–36) or a biologically active analog of GLP-1 (1–37), GLP-1 (7–37), GLP-1 (7–36) wherein said biologically active analog of GLP-1 (1–37), GLP-1 (7–37), GLP-1 (7–36) contains one or more substitutions deletions or insertions of not more than five amino acids from the amino acid sequence of GLP-1 (1–37), GLP-1 (7–37), or GLP-1 (7–36).

* * * * *

UNITED STATES PATENT AND TRADEMARK OFFICE
CERTIFICATE OF CORRECTION

PATENT NO. : 6,998,387 B1 Page 1 of 1
DATED : February 14, 2006
INVENTOR(S) : Burkhard Goke, Christoph Beglinger and Thomas R. Coolidge It is certified that error appears in the above-identified patent and that said Letters Patent is hereby corrected as shown below:

<u>Column 19,</u>
Lines 58-59, insert -- GLP-1 (7-36) in an amount effective to reduce food intake in -- between "GLP-1 (7-37)," and "a human".

Signed and Sealed this

Eighteenth Day of April, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 37
<212> TYPE: PRT
<213> ORGANISM: Unknown
<220> FEATURE:
<223> OTHER INFORMATION: Description of Unknown Organism: Mammalian GLP peptide

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: Unknown
<220> FEATURE:
<223> OTHER INFORMATION: Description of Unknown Organism: Mammalian GLP peptide

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: Unknown
<220> FEATURE:
<223> OTHER INFORMATION: Description of Unknown Organism: Mammalian GLP peptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Unknown
<220> FEATURE:
<223> OTHER INFORMATION: Description of Unknown Organism: Mammalian GLP peptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: Unknown
<220> FEATURE:
<223> OTHER INFORMATION: Description of Unknown Organism: Truncated form of GLP-1

<400> SEQUENCE: 5

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: Unknown
<220> FEATURE:
<223> OTHER INFORMATION: Description of Unknown Organism: Truncated form of GLP-1

<400> SEQUENCE: 6

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Unknown
<220> FEATURE:
<223> OTHER INFORMATION: Description of Unknown Organism: Exendin 3

<400> SEQUENCE: 7

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 31
<212> TYPE: PRT
<213> ORGANISM: Unknown
<220> FEATURE:
<223> OTHER INFORMATION: Description of Unknown Organism: Exendin 4 (9-39)NH2

<400> SEQUENCE: 8

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 9
<211> LENGTH: 39
<212> TYPE: PRT
<213> ORGANISM: Unknown
<220> FEATURE:
<223> OTHER INFORMATION: Description of Unknown Organism: Exendin 4

<400> SEQUENCE: 9

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
            35
```

<210> SEQ ID NO 10
<211> LENGTH: 38
<212> TYPE: PRT
<213> ORGANISM: Unknown
<220> FEATURE:
<223> OTHER INFORMATION: Description of Unknown Organism: Helospectrin
     I

<400> SEQUENCE: 10

```
His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
                20                  25                  30

Pro Arg Pro Pro Ser Ser
            35
```

<210> SEQ ID NO 11
<211> LENGTH: 37
<212> TYPE: PRT
<213> ORGANISM: Unknown
<220> FEATURE:
<223> OTHER INFORMATION: Description of Unknown Organism: Helospectrin
     II

<400> SEQUENCE: 11

```
His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
                20                  25                  30

Pro Arg Pro Pro Ser
            35
```

<210> SEQ ID NO 12
<211> LENGTH: 35
<212> TYPE: PRT
<213> ORGANISM: Unknown
<220> FEATURE:
<223> OTHER INFORMATION: Description of Unknown Organism: Helodermin

<400> SEQUENCE: 12

```
His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
                20                  25                  30

Pro Pro Pro
        35
```

<210> SEQ ID NO 13
<211> LENGTH: 36
<212> TYPE: PRT
<213> ORGANISM: Unknown
<220> FEATURE:
<223> OTHER INFORMATION: Description of Unknown Organism: Q8, Q9
     helodermin

<400> SEQUENCE: 13

-continued

```
His Ser Asp Ala Ile Phe Thr Glu Glu Tyr Ser Lys Leu Leu Ala Lys
1               5                   10                  15

Leu Ala Ala Leu Gln Lys Tyr Leu Ala Ser Ile Leu Gly Ser Ala Thr
            20                  25                  30

Ser Pro Pro Pro
        35
```